United States Patent [19]

Engström et al.

[11] Patent Number: 5,371,109
[45] Date of Patent: Dec. 6, 1994

[54] CONTROLLED RELEASE COMPOSITION FOR A BIOLOGICALLY ACTIVE MATERIAL DISSOLVED OR DISPERSED IN AN L2-PHASE

[75] Inventors: Sven Engström, Umeå; Kåre V. Larsson, Bjärred; Björn Lindman, Lund, all of Sweden

[73] Assignee: Drilletten AB, Malmo, Sweden

[21] Appl. No.: 107,908

[22] Filed: Aug. 18, 1993

Related U.S. Application Data

[63] Continuation of Ser. No. 643,693, Jan. 22, 1991, abandoned, which is a continuation of Ser. No. 283,926, Nov. 23, 1988, abandoned.

[30] Foreign Application Priority Data

Jul. 1, 1986 [SE] Sweden ............... 8602931-1

[51] Int. Cl.$^5$ ............................. A61K 47/00
[52] U.S. Cl. ........................ 514/786; 514/769; 514/772
[58] Field of Search ............... 424/455; 514/785, 786, 514/937, 938

[56] References Cited

U.S. PATENT DOCUMENTS

| | | | |
|---|---|---|---|
| 4,016,100 | 4/1977 | Suzuki et al. | 252/316 |
| 4,145,410 | 3/1979 | Sears | 424/450 |
| 4,235,871 | 11/1980 | Papahadjopoulos et al. | 424/450 |
| 4,241,046 | 12/1980 | Papahadjopoulos et al. | 424/450 |
| 4,328,222 | 5/1982 | Schmidt | 514/786 |
| 4,719,239 | 1/1988 | Muller et al. | 514/785 |
| 4,874,795 | 10/1989 | Yesair | 514/786 |
| 5,143,934 | 9/1992 | Lading et al. | 514/396 |

FOREIGN PATENT DOCUMENTS

0126751 12/1984 European Pat. Off.

OTHER PUBLICATIONS

Summarized Translation of Official Action from Japanese Patent Office mailed Nov. 30, 1993. for Jp. Patent Application 504060/87.
Summarized Translation of Citation 1, Japanese Patent Application Laying Open (Kokai), Application No. 53-152221, filed Dec. 9, 1978.
Summarized Translation of Citation 2, Japanese Patent Application Laying Open (Kohyo), Application No. 60-500256, filed Nov. 25, 1983.
Advances in Liquid Crystals, vol. 1, pp. 1–39 and 104–107 Per Ekwall (1975).
*Advances in Liquid Crystals*, vol. 1, pp. 1 to 109, Edited by Glenn H. Brown Academic Press, New York (1975).
"On Structural Relations Between Lipid Mesophases and Isotropic Reversed Micellar (L2) Solutions," by Krister Fontell et al.
Journal of Colloid and Interface Science, vol. 93, No. 2, pp. 453 to 460 (1983).
"Aqueous Lipid Phases of Relevance to Intestinal Fat Digestion and Absorption" by Mats Lindström et al. Lipids, vol. 19, pp. 749 to 754 (1981).

*Primary Examiner*—Raymond J. Henley, III
*Attorney, Agent, or Firm*—Burns, Doane, Swecker & Mathis

[57] ABSTRACT

The invention relates to a controlled-release composition for a biologically active material, wherein said active material has been dissolved or dispersed in an L2-phase comprising
(a) at least one monoglyceride of an unsaturated fatty acid having 16–22 carbon atoms or a vegetable or animal oil containing such a monoglyceride,
(b) at least one triglyceride of at least one unsaturated fatty acid having 16–22 carbon atoms or a vegetable or animal oil containing such triglycerides and
(c) at least one polar liquid selected from the group consisting of water, glycerol, ethylene glycol and propylene glycol. Such L2 phases are known per se but are novel in this context.

The composition is prepared by forming the L2 phase and adding the biologically active material before, during or after the formation of the L2-phase. For sensitive substances such as proteins a mixture of the mono- and triglycerides is added dropwisely to a solution of said substance in the polar liquid.

The invention also relates to the use of this specific L2-phase to encapsulate a biologically active material.

26 Claims, 1 Drawing Sheet

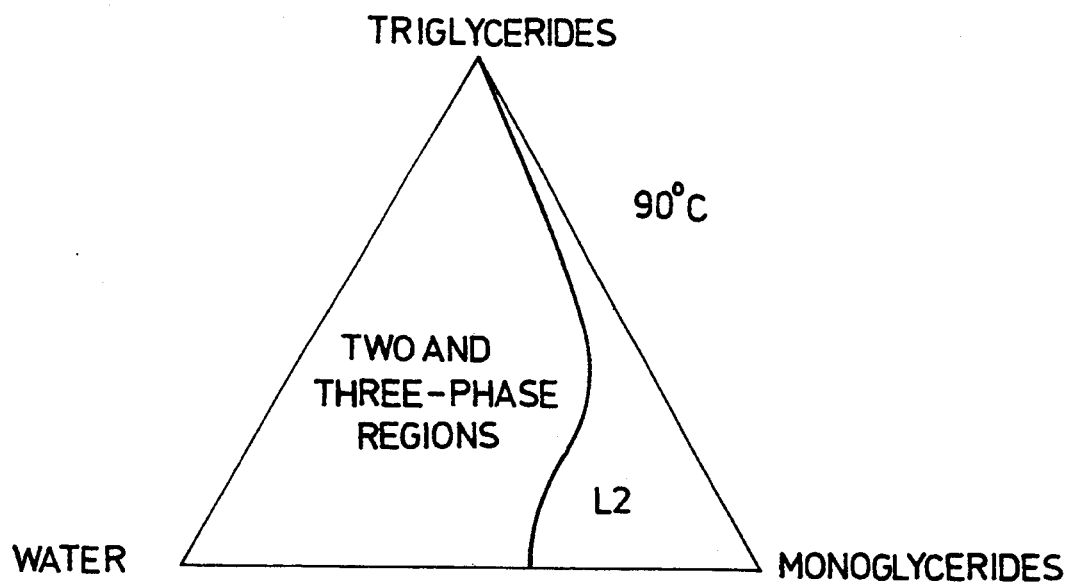
*Fig. 1*
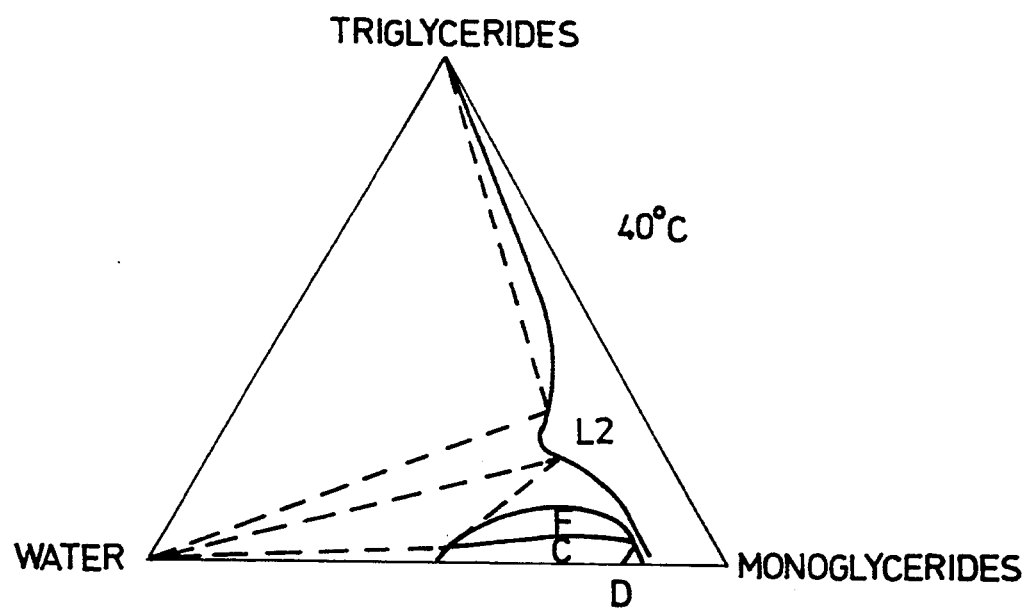

CONTROLLED RELEASE COMPOSITION FOR A BIOLOGICALLY ACTIVE MATERIAL DISSOLVED OR DISPERSED IN AN L2-PHASE

This application is a continuation of application Ser. No. 07/643,693, filed Jan. 22, 1991 now abandoned which is a continuation of application Ser. No. 07/283,926, filed Nov. 23, 1988, now abandoned.

TECHNICAL FIELD

The present invention relates to the field of encapsulating biologically active materials in order to obtain a sustained release thereof as is desirable within many different technical fields, such as for instance to have a longer lasting effect of a pharmaceutically active material. More specifically the invention relates to a novel encapsulating material or system which is thermodynamically stable, which is useful for water-soluble as well as water-insoluble biologically active compounds and which enables a highly reproducible sustained release of said biologically active compounds. With reference to last-mentioned property the term "controlled release" will be used throughout description and claims to emphasize the fact that by the present invention the desired sustained release of any active compound can be obtained in a controlled way.

BACKGROUND OF THE INVENTION

One technique of encapsulating biologically active materials for sustained-release purposed is disclosed in U.S. Pat. Nos. 4,016,100; 4,145,410; 4,235,871; and 4,241,046. In these applications polymer-water preparations or systems are utilized as encapsulating materials. These preparations are, however, thermodynamically unstable (dispersions, emulsions and vesicles) and consist of at least two phases.

The present invention is based on the use of a fundamentally different system, viz. a thermodynamically stable one-phase composition having a well-defined structure, by which it has turned out possible to eliminate or at least drastically reduce disadvantages associated with the above-mentioned prior art compositions.

The new composition or system used according to the present invention is a non-toxic liquid phase formed from certain amphiphilic substances and a polar liquid and is called an L2-phase. The L2-phase is a phase known per se but as far as we know of it has previously not been used for the purposes of the present invention. However, for a better understanding of the invention the present information can be given concerning amphiphilic substances and the L2-phase.

Amphiphilic substances are substances with hydrophilic as well as hydrophobic (lipophilic) groups and such substances spontaneously tend to self-associate in aqueous systems forming various types of aggregates. The L2-phase is one such phase. The L2-phase is a liquid phase with water-aggregates in a hydrocarbon-continuous medium (see Ekwall, P., Advances in Liquid Crystals, Ed. G. W. Brown, Academic Press, New York, 1975). The phase can coexist in equilibrium with water or a dilute aqueous solution. It is known that edible oils, like soybean oil, and water can form such a phase in the presence of monoglycerides of unsaturated fatty acids, such as sunflower oil monoglycerides (see Fontell et al. J. Colloid Interface Sci. 93 (1983) 453). Further information about L2-phases will be given below in connection with the disclosure of the invention.

BRIEF DESCRIPTION OF THE DRAWING

FIG. 1 depicts a phase diagram for the system of sunflower oil monoglyceride/soybean oil/water at 40° and 90° C.

SUMMARY OF THE INVENTION

By the present invention there is accomplished a controlled release composition for a biologically active material which composition shows several advantages as compared to the prior art compositions. As was mentioned above this is obtained by using a special L2-phase as the encapsulating material. More specifically the composition according to the present invention is characterized in that the biologically active material is dissolved or dispersed in an L2-phase comprising (a) at least one monoglyceride of an unsaturated fatty acid having 16–22 carbon atoms or a vegetable or animal oil containing such a monoglyceride, (b) at least one triglyceride of at least one unsaturated fatty acid having 16–22 carbon atoms or a vegetable or animal oil containing such triglycerides and (c) at least one polar liquid selected from the group consisting of water, glycerol, ethylene glycol and propylene glycol.

The above-mentioned L2-phase is advantageous for the purposes according to the invention inter alia for the following reasons:

It is thermodynamically stable and therefore, it has no tendency to phase separate with time (unless chemical decomposition occurs).

It has distinct hydrophilic and hydrophobic domains, which enables it to dissolve (solubilize) or disperse both water-soluble and water-insoluble compounds.

The distinct hydrophilic and hydrophobic domains represent an organized structure that puts restrictions on the diffusion of added compounds, a fact which can be advantageously used for controlled-release purposes. Thus, the release rate of a bioactive substance is determined by the outer surface of the phase towards the surrounding medium and the proportions between hydrophilic and hydrophobic domains within the phase. As was mentioned above the L2-phase used in accordance with the present invention comprises or consists of a special liquid monoglyceride, a special liquid triglyceride and a polar liquid. Once these three components of the system have been specified in each single case, the exact composition of the corresponding L2-phase can be found in the prior art, e.g. from a ternary phase diagram. An example of such a phase diagram is shown in FIG. 1 of the drawing which shows the phase diagram for the system of sunflower oil monoglyceride/soybean oil/water at 40° C. and 90° C. The two-phase regions and three-phase triangles are marked only at 40° C. Notations: L2, isotropic "oily" solutions; C, cubic liquid crystalline phase; D, lamellar liquid crystalline phase; F, reversed hexagonal liquid-crystalline phase. Concentrations in % (w/w). At room temperature the L2-phase has a maximum content of water of about 12–14% (w/w), and substances localized in the aqueous regions or aggregates will have a highly reproducible sustained release into an outside water phase (or polar liquid phase, respectively).

Generally, the monoglyceride is a monoglyceride of an unsaturated fatty acid having 16–22 carbon atoms. However, often it is not necessary or rather preferable not to utilize said monoglyceride in the pure form but to use instead a natural product containing the same, such as a vegetable or animal oil containing the desired monoglyceride.

According to a preferable embodiment of the composition of the invention the monoglyceride is a monoglyceride of an unsaturated fatty acid having 18 carbon atoms or a vegetable or animal oil containing the same. An especially preferable monoglyceride from this group is monoolein or monolinolein or a vegetable or animal oil containing the same.

The triglyceride used is a triglyceride of at least one unsaturated fatty acid having 16–22 carbon atoms but also in this case a natural product containing said triglyceride can replace the same, such as a vegetable or animal oil containing the desired triglyceride.

A preferred composition according to the invention contains as said triglyceride a triglyceride of at least one unsaturated fatty acid having 18 carbon atoms or a vegetable or animal oil containing the same, an especially preferable oil being soybean oil.

The polar liquid utilized in the claimed composition is preferably water, but said water can also be partly or fully replaced by glycerol, ethylene glycol and/or propylene glycol, which polar liquids can be used for fine adjustments of the release rates of biologically active materials from the L2-phase. That is different polar liquids or different proportions between polar liquids can be used to control the release rate of a specific active material. For such a control or adjustment of the release rate common salt, i.e. sodium chloride, can also be used.

As was mentioned above the exact composition of a specific L2-phase is taken from a phase diagram while taking into consideration the desired release rate for the active compound to be encapsulated, which rate is determined by a person skilled in the art by simple routine experiments. However, a preferable weight ratio of monoglyceride to triglyceride is within the range of from 1:1 to 3:1, more preferably from 2:1 to 2,5:1 and especially around 7:3. The content of water (or other polar liquid) is generally determined by the maximum water content of the L2-phase region, which is often not above 12–14% (w/w). Therefore, a suitable water content is within the range of 4–12, preferably 5–10%.

With reference to the term "biologically active material" or similar as used throughout the specification and claims it means a compound or composition which when present in an effective amount, reacts with and/or affects living cells and organisms.

One interesting group of compounds to be encapsulated in accordance with the present invention is the group of pharmaceutical compounds, e.g. antibiotics, proteins, steroids, vitamins and nucleic acids, penicillin being an example of antibiotic, insulin an example of a protein and oestriol and prostaglandins examples of steroids.

In connection with proteins it can also be mentioned that an L2-phase exists in connection with fat digestion and absorption in the intestine (see Lindström et al., Lipids 19, 1981, 749). We have found that this L2-phase can protect sensitive substances, like peptides, from degradation in the gastric environment until they are absorbed. Furthermore, an increased uptake has been observed. This L2-phase can function as a vehicle providing chemical protection and controlled uptake in oral administration of drugs and, thus, in certain cases even an improved uptake in the intestinal system.

The composition according to the invention when used as a pharmaceutical composition is prepared with a carrier suitable for oral, rectal or transdermal administration or suitable for inhalation.

Another example of a biologically active material to be encapsulated in accordance with the principles of the present invention is a compound for agricultural use, such as pesticides, fertilizers and trace elements.

Still another example of an interesting active compound in this connection is a feromone but any active substance that can be dissolved or dispersed in the L2-phase should be encapsulable in accordance with the invention.

Generally, the biologically active material is present in an amount of 0,1–10% by weight of a ready-to-use composition, although the invention is not limited to said amounts.

According to another aspect of the invention a method of preparing the above-mentioned controlled-release composition is provided. This method is characterized by forming a mixture of the above-defined monoglyceride and triglyceride in such amounts thereof that an L2-phase is formed when said mixture is contacted with the polar liquid selected from the group consisting of water, glycerol, ethylene glycol and propylene glycol, the biologically active material being added before, during or after the formation of said L2-phase. Generally this means that said active material is added to the L2-phase when formed but it can also be added e.g. to the polar liquid before said L2-phase is formed.

Before disclosing some preferable embodiments of the method according to the invention the following should be noted. Since water is the preferable polar liquid some aspects or embodiments of the invention will be described in connection with water. However, this does not mean that the general ideas are not similarly applicable to the other polar liquids mentioned. The water aggregates of the L2-phase of the interfacial zone between the hydrophilic and hydrophobic regions of the phase provide the sites of controlled release in the case of active substances solved in the phase. In the case of a very low solubility of the active substance in the phase it can be dispersed within the L2-phase. The L2-phase has a very low interfacial tension towards an outside water phase, and it is therefore easily emulsified into water. When a sensitive substance, e.g. a protein, is solubilized into the L2-phase, it must first be solved in the water phase. Then the protein solution is mixed with the monoglyceride-triglyceride mixture, the optimum weight ratio of last-mentioned mixture being 7:3, said mixing operation being performed by dropwisely adding the monoglyceride-triglyceride liquid to the protein solution. Only under these conditions it is possible to keep the native protein structure. If the drops are added to the protein solution with intervals around one second, the L2-phase formed will swell to the limit of water swelling between each addition. Thus the protein will keep the water environment needed during the whole preparation process.

Thus, one embodiment of the claimed method, which is of special interest in connection with sensible substances, such as proteins, is characterized by forming a solution of the active material in the polar liquid, preferably water, as well as a mixture of the monoglyceride and the triglyceride and adding the monoglyceride-triglyceride mixture dropwisely to the solution of said active material in the polar liquid.

The preparation in this way of a 5% (w/w) cytochrome c solution in water, which is then transferred into an L2-phase formed by monolein-soybean oil (weight 7:3) gives a final protein concentration in the L2-phase of 0.6%. When this L2-phase is kept in contact with a water phase, with 1 cm$^3$ of each phase and 1 cm$^2$ in contact area in between, it takes about two days until the protein concentration in the outside water has reached the equilibrium value.

The preparation of L2-phase containing bioactive substances of more simple types, like hydrocortisone or vitamins, can be prepared by mere mixing of the ingredients in the desired proportions. Then it is just to wait for equilibrium to be reached, as the L2-phase is thermodynamically stable.

With reference to the method according to the invention it should also be added that those preferable embodiments which have been described above in connection with the composition are similarly applicable to the method and need not be repeated here.

Finally, the present invention also relates to the use of the above-mentioned L2-phase, including all preferable embodiments thereof, to encapsulate a biologically active material in order to obtain a preparation giving a controlled release of said biologically active material. As has been mentioned above this use is especially interesting in connection with sensible substances such as proteins.

EXAMPLES

Some embodiments of the invention will now be described more in detail by the following non-limiting examples.

EXAMPLE 1

100 mg of lysozyme is dissolved in 1 g of water. This solution is mixed at 40° C. with a mixture of 3 g of soybean oil and 7 g of sunflower oil monoglycerides last-mentioned mixture being dropwisely added to said lysozyme solution. The L2-phase formed thereby exhibits a slow release of the protein molecules into water in the environment. A droplet thereof under the eye-lid will provide an antimicrobial effect during several hours.

EXAMPLE 2

1 g of hydrocortison is dissolved in an L2-phase prepared from 65 g of monoolein, 27 g of olive oil, 5 g of propylene-glycole and 3 g of water. This liquid can be used for a transdermal administration of hydrocortison.

EXAMPLE 3

Benzylpenicillin is used in the form of a saturated water solution to form an L2-phase which consists of 13% (w/w) of penicillin solution, 60% of monoolein and 27% (w/w) of soybean oil. The ingredients are mixed at room temperature until a transparent single phase is obtained. The penicillin is protected against acidic degradation in the stomach.

We claim:

1. A controlled-release composition for a biologically active material comprising (1) an added biologically active material dissolved or dispersed in (2) an L2-phase comprising (a) at least one monoglyceride of an unsaturated fatty acid having 16–22 carbon atoms, a vegetable oil comprising such a monoglyceride or an animal oil comprising such a monoglyceride, (b) at least one triglyceride of at least one unsaturated fatty acid having 16–22 carbon atoms, a vegetable oil comprising such a triglyceride or an animal oil comprising such a triglyceride and (c) at least one polar liquid selected from the group consisting of water, glycerol, ethylene glycol and propylene glycol, said monoglyceride, triglyceride, and polar liquid being present in proportions which will form an L2-phase and said biologically active material being of such a nature that it is dissolved or dispersed in a polar liquid aggregate or in an interfacial zone between hydrophilic and hydrophobic regions of said L2-phase, whereby said biologically active material is released in a controlled way when said composition is in contact with a surrounding phase of polar liquid.

2. A composition according to claim 1 wherein said monoglyceride is a monoglyceride of an unsaturated fatty acid having 18 carbon atoms, a vegetable oil comprising the same or an animal oil comprising the same.

3. A composition according to claim 2 wherein said monoglyceride is selected from the group consisting of monoolein, monolinolein, a vegetable oil comprising the same and an animal oil comprising the same.

4. A composition according to claim 1 wherein said triglyceride is a triglyceride of an unsaturated fatty acid having 18 carbon atoms, a vegetable oil comprising the same or an animal oil comprising the same.

5. A composition according to claim 4 wherein said triglyceride is soybean oil.

6. A composition according to claim 1 wherein the weight ratio of monoglyceride to triglyceride is within the range of from 1:1 to 3:1.

7. A composition according to claim 1 wherein the biologically active material is selected from the group consisting of pharmaceutical compounds; compounds for agricultural uses; and feromones.

8. A composition according to claim 1 wherein said composition is ready-to-use and wherein the biologically active material is present in an amount of 0.1–10% by weight of said ready-to-use composition.

9. A composition according to claim 1 including a water content of about 4–12% by weight.

10. A composition according to claim 1 including sodium chloride as a release rate modifying agent.

11. A pharmaceutical composition according to claim 1 including a pharmaceutically acceptable carrier for oral, rectal or transdermal administration or for inhalation.

12. A composition according to claim 6 wherein the weight ratio of monoglyceride to triglyceride is within the range of from 2:1 to 2.5:1.

13. A composition according to claim 12 wherein the weight ratio of monoglyceride to triglyceride is about 7:3.

14. A composition according to claim 7 wherein said pharmaceutical compounds are antibiotics, proteins, steroids, vitamins, or nucleic acids.

15. A composition according to claim 7 wherein said compounds for agricultural uses are pesticides, fertilizers, or trace elements.

16. A composition according to claim 9 including a water content of about 4–12% by weight.

17. A controlled-release composition for a protein comprising (1) an added protein dissolved or dispersed in 2) an L2-phase comprising (a) at least one monoglyceride of an unsaturated fatty acid having 16–22 carbon atoms, a vegetable oil comprising such a monoglyceride or an animal oil comprising such a monoglyceride, (b) at least one triglyceride of at least one unsaturated fatty acid having 16–22 carbon atoms, a vegetable oil comprising such a triglyceride or an animal oil comprising such a triglyceride and (c) at least one polar liquid selected from the group consisting of water, glycerol, ethylene glycol and propylene glycol, said monoglyceride, triglyceride, and polar liquid being present in proportions which will form an L2-phase and said protein being of such a nature that it is dissolved or dispersed in a polar liquid aggregate or in an interfacial zone between hydrophilic and hydrophobic regions of said L2-phase, whereby said protein is released in a controlled way when said composition is in contact with a surrounding phase of polar liquid.

18. The controlled release composition of claim 1 further comprising, in addition to said L2-phase including an added biologically active material, a polar liquid outside phase into which said active material is released.

19. A pharmaceutical composition comprising (i) the L2-phase including an added biologically active material as defined by claim 1 and (ii) a carrier suitable for oral, rectal, or transdermal administration or for inhalation.

20. A method of controlledly releasing an active agent into or on a biological system comprising contacting said system with the composition of claim 1, optionally in a suitable carrier.

21. The method of claim 20 wherein said system is the intestine.

22. The method of claim 21 wherein said composition is contacted with the intestine by administering said composition orally to a patient.

23. The method of claim 20 wherein said system is the rectum.

24. The method of claim 20 wherein said system is the skin.

25. The method of claim 20 wherein said system is contacted with said composition by inhalation.

26. A controlled-release composition for a biologically active material comprising (1) an added biologically active material dissolved or dispersed in (2) an L2-phase comprising (a) at least one monoglyceride of an unsaturated fatty acid having 16–22 carbon atoms, a vegetable oil comprising such a monoglyceride or an animal oil comprising such a monoglyceride, (b) at least one triglyceride of at least one unsaturated fatty acid having 16–22 carbon atoms, a vegetable oil comprising such a triglyceride or an animal oil comprising such a triglyceride and (c) at least one polar liquid selected from the group consisting of water, glycerol, ethylene glycol and propylene glycol, said monoglyceride, triglyceride and polar liquid being present in proportions which will form an L2-phase and said biologically active material being released in a controlled way when said composition is in contact with a surrounding phase of polar liquid.

* * * * *